United States Patent
Mullinax et al.

[11] Patent Number: 6,066,446
[45] Date of Patent: May 23, 2000

[54] ASSAY MEMBER AND METHOD FOR ITS MANUFACTURE

[75] Inventors: Thomas R. Mullinax, Newton; Mark N. Bobrow, Lexington; Michael E. Bembenek, Burlington, all of Mass.

[73] Assignee: NEN Life Science Products, Inc., Boston, Mass.

[21] Appl. No.: 09/353,515

[22] Filed: Jul. 14, 1999

Related U.S. Application Data

[63] Continuation-in-part of application No. 09/212,211, Dec. 16, 1998, Pat. No. 5,972,595.
[60] Provisional application No. 60/068,244, Dec. 19, 1997.
[51] Int. Cl.[7] .............................. C12Q 1/00; C12Q 1/44; C12Q 1/16
[52] U.S. Cl. ............................ 435/4; 435/19; 435/18; 435/21; 435/968; 435/283.1; 435/35
[58] Field of Search ................... 435/4, 19, 18, 435/21, 968, 283.1, 35

[56] References Cited

U.S. PATENT DOCUMENTS

| | | | |
|---|---|---|---|
| 3,654,090 | 4/1972 | Schuurs et al. | 195/103.5 |
| 4,444,879 | 4/1984 | Foster et al. | 435/7 |
| 4,446,232 | 5/1984 | Liotta | 435/7 |
| 4,530,900 | 7/1985 | Marshall | 435/7 |
| 4,629,688 | 12/1986 | Bolguslaski et al. | 435/7 |
| 4,654,299 | 3/1987 | Lentfer | 435/7 |
| 4,668,623 | 5/1987 | Rinnunen et al. | 435/19 |
| 4,937,188 | 6/1990 | Giese et al. | 435/41 |
| 5,104,815 | 4/1992 | Garner et al. | 436/505 |
| 5,190,864 | 3/1993 | Giese et al. | 435/41 |
| 5,198,493 | 3/1993 | Holmberg et al. | 525/54.1 |
| 5,238,817 | 8/1993 | Bobrow et al. | 435/28 |
| 5,258,041 | 11/1993 | Guire et al. | 623/66 |
| 5,263,992 | 11/1993 | Guire | 623/66 |
| 5,304,465 | 4/1994 | Garland et al. | 435/4 |
| 5,328,831 | 7/1994 | Stewart et al. | 435/12 |
| 5,512,329 | 4/1996 | Guire et al. | 427/508 |
| 5,610,287 | 3/1997 | Nikiforov et al. | 536/24.3 |
| 5,688,642 | 11/1997 | Chrisey et al. | 435/6 |
| 5,741,551 | 4/1998 | Guire et al. | 427/407.1 |
| 5,874,569 | 2/1999 | Elsner et al. | 536/51 |
| 5,900,481 | 5/1999 | Lough et al. | 536/55.3 |
| 5,972,595 | 10/1999 | Kasila et al. | 435/4 |
| 5,989,854 | 11/1999 | Cook | 435/35 |

OTHER PUBLICATIONS

Camps et al. (1992) Stimulation of phospholipase C by guanine–nucleotide–binding protein βγ subunits. Eur. J. Biochem., 206:821–831.

Camps et al. (1990) Guanosine 5'–ly–thio triphosphate–stimulated hydrolysis of phosphatidylinositol 4,5–bisphosphate in HL–60 granulocytes. Biochem, J., 271:743–748.

Crooke and Bennett (1989) Mannalian phosphoinositide–specific phospholipase C isoenzymes. Cell Calcium, 10:309–323.

De Vivo (1994) Assays for G–protein regulation of phospholipase C activity. Methods in Enzymology, 238:131–141.

Gierschik et al. (1989) Dual Mg2+ control of formyl–peptide–receptor–G–protein interaction in HL 60 cells Evidence that the low–agonist–affinity receptor interacts with and activates the G–protein. Eur. J. Biochem., 183:97–105.

Haber et al. (1991) Activation of phosphoinositide–specific phospholipase C from rat liver by polyamines and basic proteins. Arch. Biochem. Biophys., 288(1):243–249.

Hianik et al. (1996) Immobilization of enzymes on lipid bilayers on a metal support allows study of the biophysical mechanisms of enzymatic reactions. Bioelectrochemistry and Bioenergetics, 41:221–225.

(List continued on next page.)

*Primary Examiner*—Louise N. Leary
*Attorney, Agent, or Firm*—Gifford, Krass, Groh, Sprinkle, Anderson & Citkowski, P.C.

[57] ABSTRACT

Disclosed is a member comprising an interactive material which is covalently bonded to a support body by a linker material. The member can be used as a part of an assay, and the support body may include a scintillator material.

22 Claims, 4 Drawing Sheets

OTHER PUBLICATIONS

Hoekstra and Duzgunes (1993) Lipid mixing assays to determine fusion in liposome systems. Methods in Enzymology, 220:15–32.

Miller and Racker (1976) Fusion of phospholipid vesicles reconstituted with cytochrome c oxidase and mitochondrial hydrophobic protein. J. Membr. Biol., 26:319–333.

Mueller et al. (1962) Reconstitution of excitable cell membrane structure in vitro. Circulation, 26:1167–1177.

Ottova and Tien (1997) Self–assembled bilayer lipid membranes: from mimicking biomembranes to practical applications. Bioelectrochemistry and Bioenergetics, 42:141–152.

Rhee and Choi (1992) Regulation of inositol phospholipid–specific phospholipase C isozymes. J. Biol. Chem., 267(18):12393–6.

Wright and Huang (1992) Bilayer stabilization of phosphatidylethanolamine by N–biotinylphosphatidylethanolamine. Biochim. Biophys. Acta, 1103:172–178.

Ahluwalia et al. (1992) A comparative study of protein immobilization techniques for optical immunosensors. Biosensores & Bioelectronics, 7(3):207–14, Abstract.

Bhatia et al. (1989) Use of thiol–terminal silanes and heterobifunctional crosslinkers for immobilization of antibodies on silica surfaces. Analytical Biochemistry, 178(2):408–13, Abstract.

Blanchard et al. (1990) Regeneration of immunosorbent surfaces used in clinical, industrial and environmental biosensors. Journal of Immunological Methods, 130:263–275.

Chan and Nie (1998) Quantum dot bioconjugates for ultrasensitive nonisoptopic detection. Science, vol. 281, pp. 2016–2018.

Chemla et al. (1986) Covalent binding of proteins and its uses. Journal of Immunological Methods, 94(1–2):263–9. Abstract.

Collioud et al. (1993) Oriented and covalent immobilization of target molecules to solid supports: synthesis and application of light–activatable and thiol–reactive cross–linking reagent. Bioconjugate Chemistry, 4(6):528–36. Abstract.

Elsner and Mouritsen (1994) Use of psoralens for covalent immobilization of biomolecules in solid phase assays. Bioconjugate Chemistry, 5(5):463–7, Abstract.

Fischer et al. (1977) Immobilization of proteins on macroporous glasses involving maleinimide as the anchoring group. (German) Acta Biologica et Medica Germanica, 36(7–8):999–1005, Abstract.

Gao et al. (1994) Photolinker–polymer–mediated immobilzation of monoclonal antibodies, F(ab')2 and F(ab') fragments. Biotechnology & Applied Biochemistry, 20(Pt 2):251–63, Abstract.

Ghosh and Musso (1987) Covalent attachment of oligonucleotides to solid supports. Nucleic Acids Research, 15(13):5353–72, Abstract.

Hofstetter et al. (1997) Direct binding of low molecular weight haptens to Elisa plates. Journal of Immunological Methods, 210(1):89–92, Abstract.

"Immobilized Enzymes" (Book) (1980), Carr & Bowers, editors, John Wiley & Sons, vol. 56, pp. 165–181.

Joos et al. (1997) Covalent attachment of hybridizable oligonucleotides to glass supports. Analytical Biochemistry, 247:96–101.

Larsson et al. (1997) Covalent binding of proteins to grafted plastic surfaces suitable for immunoassays. II. Picograms of IgE detected in BAL fluid in sarcoidosis. Journal of Immunological Methods., 210:41–49.

Larsson et al. (1987) Covalent binding of proteins to grafted plastic surfaces suitable for immunoassays. Journal of Immunological Methods, 98:129–135.

Lutz et al. (1990) Covalent binding of detergent–solubilized membrane glycoproteins to "Chemobond" plates for Elisa. Journal of Immunological Methods, 129:211–220.

Mirsky et al. (1997) Capacitive monitoring of protein immobilization and antigen–antibody reactions on monomolecular alkylthiol films on gold electrodes. Biosensors & Bioelectronics, 12(9–10):977–89, Abstract.

Nelson et al. (1997) Surface plasmon resonance biomolecular interaction analysis mass spectrometry. 2. Fiber optic–based analysis. Analytical Chemistry, 69(21):4369–74, Abstract.

Oroskar et al. (1996) Detection of immolbilized amplicons by Elisa–like techniques. Clinical Chemistry, 42(9):1547–55, Abstract.

Rauterberg et al. (1984) Optimal conditions for the preparation of ferritin–labeled antibodies defined by binding to their antigen in an Elisa. Immunobiology, 166(4–5):439–45, Abstract.

Romer and Rauterberg (1984) Enzyme–linked immunosorbent assay (Elisa) with covalently bound protein on glass tubes: 1. Stable antigenicity and binding of IgG as a model antigen after repeated use. Immunobiology, 166(1):24–34, Abstract.

Rotmans and Delwel (1983) Cross–linking of Schistosoma mansoni antigens and their covalent binding on the surface of polystyrene microtitration trays for use in the Elisa. Journal of Immunological Methods, 57(1–3):87–98, Abstract.

Schossler et al. (1985) The use of glass as solid phase in enzyme immunoassay as exemplified by the detection of circulating immune complexes. Biomedica Biochimica Acta., 44(7–8):1247–53, Abstract.

Solomon et al. (1992) Microalbuminuria immunoassay based on antibodies covalently conjugated to Eupergit C–coated beads. Diabetes Care, 15(11):1451–4, Abstract.

Stabel et al. (1992) Anti–IgG immobilized controlled–pore glass. Thionyl chloride–activated succinamidopropyl–glass as a covalent immobilization matrix. Applied Biochemistry & Biotechnology, 36(2):87–96, Abstract.

Subramanian and Velander (1996) Effect of antibody orientation on immunosorbent performance. Journal of Molecular Recognition, 9(5–6):528–35, Abstract.

Williams and Blanch (1994) Covalent immobilization of protein monolayers for biosensor applications. Biosensors & Bioelectronics, (2):159–67, Abstract.

Wood and Gadow (1983) Immobilisation of antibodies and antigens on macro solid phases—a comparison between adsorptive and covalent binding. A critical study of macro solid phases for use in immunoassay systems. Part 1. Journal of Clinical Chemistry & Clinical Biochemistry, 21(12):789–97, Abstract.

PLC δ 1 Activity in the Presence and Absence of Additives on [$^3$H] PIP$_2$ Coated Phospholipid Support Plate PLC δ 1 Activity in the Presence and Absence of Additives on [$^3$H] PIP$_2$ Coated Phospholipid Support Plate

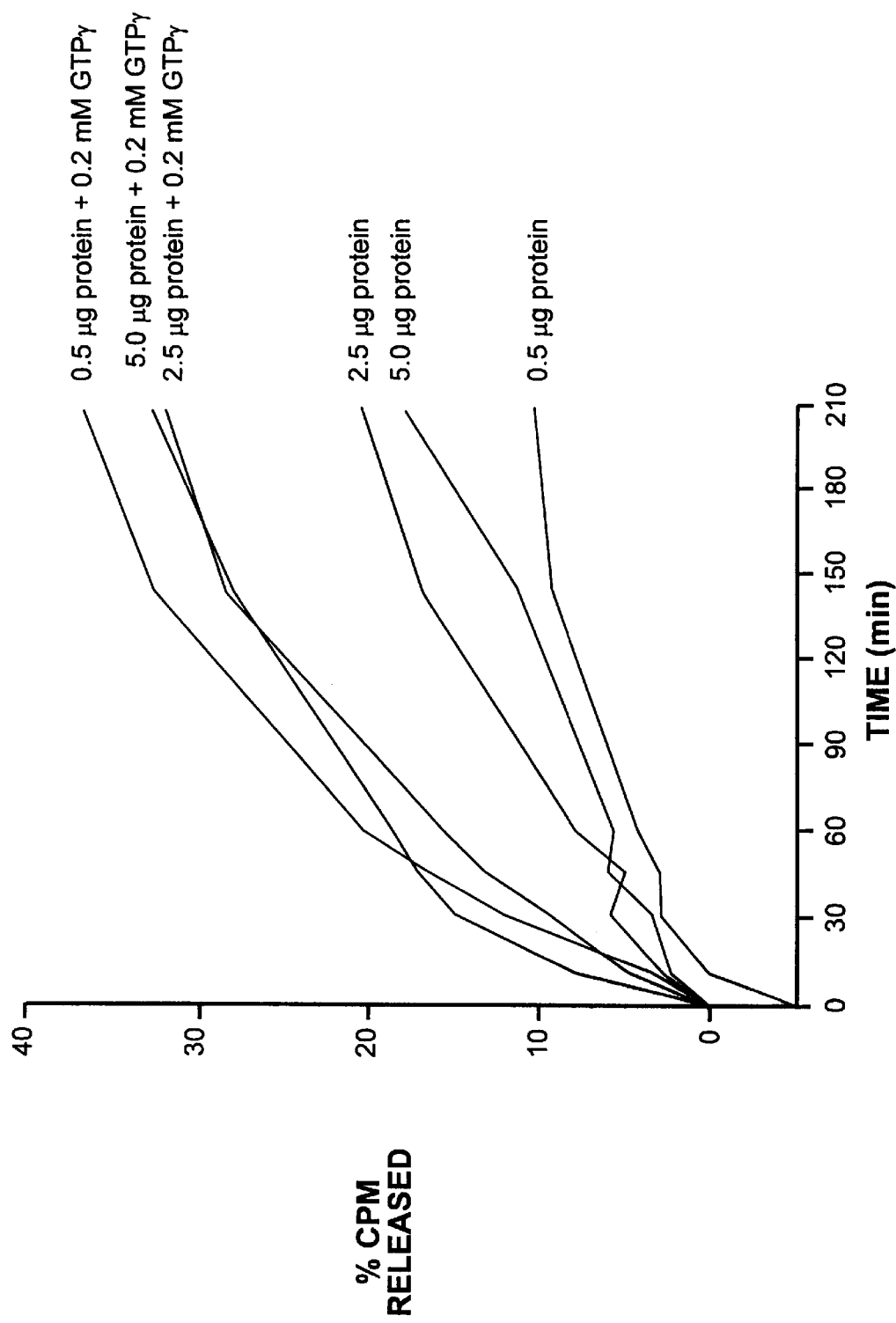

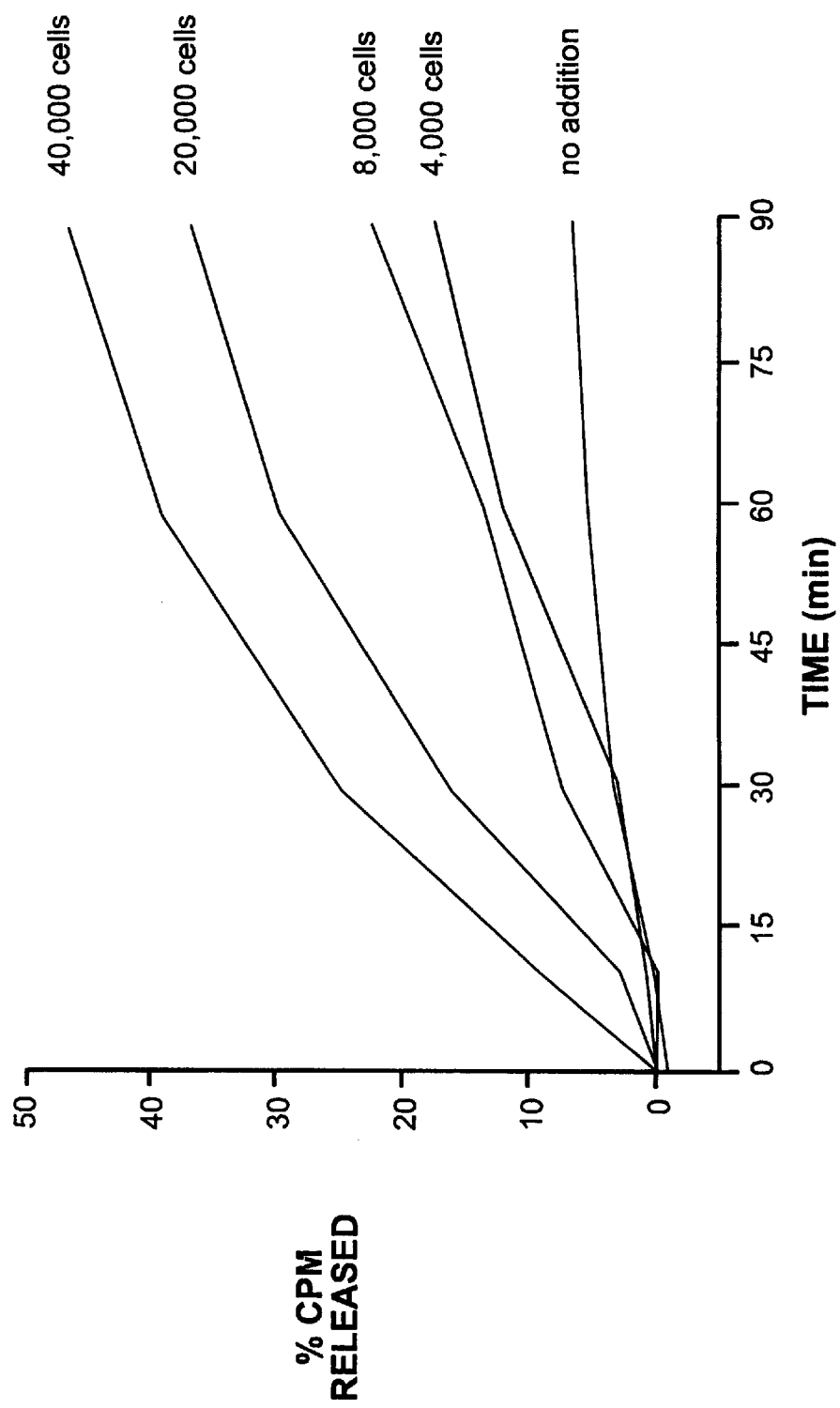

ASSAY MEMBER AND METHOD FOR ITS MANUFACTURE

This application is a continuation-in-part of U.S. patent application Ser. No. 09/212,211 entitled "An Enzyme Assay using a Solid Phase Substrate" filed on Dec. 16, 1998 now U.S. Pat. No. 5,972,595 and claiming priority of U.S. Provisional Application No. 60/068,244 filed Dec. 19, 1997.

FIELD OF THE INVENTION

This invention relates generally to methods and materials for binding an interactive material to a support body. More specifically the invention relates to assay members comprised of a support body having an interactive material retained thereupon. Most specifically the invention relates to an assay member having an interactive material covalently bonded thereto by a linking material.

BACKGROUND OF THE INVENTION

Many chemical and biochemical assays employ an interactive material which is retained upon a support member. In the context of this disclosure, an interactive material is meant to include a material which, in at least one step of the assay, interacts with other chemical components of the assay. The interaction can comprise a binding reaction, or a reaction which generates new chemical species or which alters the configuration of a chemical species. The interactive materials can comprise molecular materials, macro molecular materials, or assemblages of species such as membranes, layered structures and other molecules that interact with chemical components of the assay. For example, the interactive material can include antibodies, antigens, enzymes or other catalytic species, substrates for the enzymes, reducing agents, oxidizing agents, proteins, nucleic acids, lipid structures, receptors, membranes, carbohydrates and various polymeric materials.

Frequently, at least one interactive material in a chemical reaction is retained upon a support member which may comprise a plate, a body of beads or other particulate material, tubes, rings, a porous matrix or other material of various designs. Within the context of this disclosure, any such support structure will be referred to as a support body. One particularly important class of support bodies comprise those bodies having a scintillator material incorporated thereinto. As is known in the art, a scintillator material generates light in response to energy input, most typically from a particle or high energy photon generated in a radiochemical decay process. Scintillator coated supports are frequently used in combination with radio chemical agents for a variety of assay procedures wherein light generated by the scintillator support, is indicative of the presence or amount of specific materials.

In general, the prior art has implemented a variety of approaches towards retaining interacting materials on support bodies. Any such methods must adequately secure the interactive material to this support so that it will be retained thereupon throughout storage and use of the coated support as is necessary. In the prior art, interactive materials have been retained on a support, by hydrophilic/hydrophobic interactions, or physical processes such as adsorption and the like. In some instances, a support body is coated with a material which facilitates adhesion of the interactive material. In some instances, materials have been bonded to supports through covalent binding; however, such prior art techniques required pretreatment of the support, or the interactive material, under fairly extreme conditions in order to provide chemically modified sites through which covalent bonding is accomplished. For example, $^{60}Co$ irradiation has been employed to graft carboxyl groups onto a polymeric assay plate in order to modify the plate so that proteins can be subsequently affixed thereto by EDAC activated covalent binding. (Larssen et al. 1987). Such surface modification steps are costly and difficult to implement. Therefore, there is a need for the methods of the present invention, which permit interactive materials to be covalently retained upon supports without the need for irradiating, grafting, chemically modifying or otherwise pretreating the support or the interactive material. Any materials or methods used to affix the interactive material to a support body must not interfere with the intended use of the interactive material or the resultant combination. This presents a significant problem when scintillator support bodies are employed, since a number of materials can quench scintillation or otherwise interfere with the use of the substrate.

As will be explained in greater detail herein below, the present invention is directed to methods and materials wherein an interactive material is retained on a support body by covalent interaction with, or initiated by, a linker material. The linker material is selected to covalently bind to the interactive material and to also be capable of binding, by covalent binding or otherwise, to the support body. Alternatively, the linker material will cause the interactive material to covalently bind to the support, while it, itself, is not incorporated in the final bond. In such instances, the linker material is akin to a catalyst. Within the context of this disclosure, the interactive material is still considered to be covalently bonded to the support by the linker, since the linker causes and participates in the binding. Covalent binding is a chemical binding wherein a bond is created by the sharing of electrons between atoms, and as such, is distinguished from physical processes such as absorption, and from other types of chemical bonds such as purely ionic bonds. It is to be understood that, in accord with chemical bonding theory, covalent bonds can have some degree of ionic character and still be considered covalent bonds; accordingly, within the context of this disclosure, covalent bonds are to be understood to be bonds in which there is some degree of electron sharing, even though there may be some degree of ionic character in that bond.

The methods and materials of the present invention provide for the efficient attachment of a variety of interactive materials to various substrates. It is significant that the attachment materials and methods of the present invention may be employed in those instances where scintillator support bodies are utilized, and will not adversely affect the use of such supports. The materials and methods of the present invention may be employed in connection with a variety of applications wherein interactive materials are retained upon support bodies, and one application comprises assays. One type of assay in which the present invention has particular utility is an enzyme assay wherein a substrate for the enzyme is immobilized upon a support body. One specific type of such assay utilizes a synthetic membrane as a substrate, and the present invention is readily employed to attach such synthetic membrane materials to a variety of support bodies including scintillator support bodies.

Because many intracellular and intercellular processes are membrane mediated, there has been a great deal of research on the reconstitution of biological membranes as a method to study these processes. Since the original development of a procedure to form artificial planar phospholipid bilayer membranes (Mueller et al., 1962) and the demonstration of the fusion of vesicles that contain ion channels to planar membranes (Miller and Racker, 1976), studies have employed a variety of artificial membrane systems and various methods for studying functional molecules that are incorporated in or bound to biological membranes (Hoekstra and Duzgunes, 1993). Some researchers have incorporated biotinylated lipids (e.g., see Wright and Huang, 1992) or functional enzymes (e.g., see Hianik et al., 1996) into artificial membranes, but the purpose has been to study properties of the membranes or the incorporated molecules, not to use the synthetic membranes as a tool to study the properties of exogenous molecules as in the present invention. For a review of current techniques and research in this area see Ottova and Tien, 1997.

Phospholipase C (PLC) is a generic name for enzymes that catalyze the hydrolysis of phosphoglycerides into diacylglycerols and phosphorylated alcohols such as serine, choline, inositol, glycerol, or ethanolamine. For example, a specific phospholipase C hydrolyzes phosphatidylinositol-4-phosphate (PIP) or phosphatidylinositol-4,5-bisphosphate ($PIP_2$), resulting in each case in the formation of two second messengers: a hydrophobic diacylglycerol and a hydrophilic inositol phosphate ($IP_2$ or $IP_3$ respectively). This hydrolysis can be monitored by a variety of methods using endogenously or exogenously labeled substrates.

De Vivo (1994) describes current methods used for measuring the hydrolysis of $PIP_2$. In the endogenous substrate approach, the cells of interest are cultured in the presence of myo-$[^3H]$-inositol. The cells convert inositol to phosphatidylinositol (PI) using phosphatidylinositol synthase, and the PI in turn is converted to PIP-$[^3H]$ and $PIP_2$-$[^3H]$ by phosphatidylinositol kinases. When the polyphosphoinositide pool is labeled to a steady state, the breakdown of PIP and $PIP_2$ is initiated by the addition to the cell culture medium of an appropriate stimulatory factor (e.g., receptor agonists for intact cells or guanylyl nucleotides for permeabilized cells).

In the exogenous substrate approach, purified labeled phospholipids are used as the substrate. The phospholipids are mixed in the presence or absence of detergent and sonicated briefly on ice to prepare vesicles. Aliquots of the substrate are mixed with a source of PLC (membranes or purified enzyme) and, often, G-protein subunits.

In both the endogenous and exogenous substrate approaches, solvent extraction is used to separate the hydrophilic reaction products from the hydrophobic substrate. Current methods for sphingomyelinase assays also require solvent extraction steps. It would be desirable to eliminate the extraction step for environmental and health reasons. In addition, it is difficult to automate the extraction of large numbers of samples, as would be necessary for example in high throughput screening of drug candidates.

SUMMARY OF THE INVENTION

There is disclosed herein the assay member of the type which comprises a support body having an interactive material covalently bonded thereto by a linker material. The linker material may covalently bind to the interactive material, and/or to the support; or it may cause the interactive material to covalently bind to the support.

In particular instances, the interactive material can be a member of a bonding pair, and such interactive materials can include proteins, nucleic acids, lipids and receptors. In other particular instances, the support body can be a scintillator support. A linker can further be capable of covalently binding to the support member, or it can be retained thereupon by other binding processes. In some particular instances, the linker can be a vinylsulfone, a carbodiimide, or a photochemically activatable compound capable, when activated, of covalently binding to, or causing the covalent binding of, the interactive material.

In some particular instances, the interactive material can comprise phosphatidylethanolamine, streptavidin or wheat germ agglutinin.

The present invention also includes methods for covalently binding interactive materials to support bodies.

BRIEF DESCRIPTION OF THE DRAWINGS

Other advantages of the present invention will be readily appreciated as the same becomes better understood by reference to the following detailed description when considered in connection with the accompanying drawings wherein:

FIG. 3 is a graph illustrating the stimulation of PLC activity by addition of GTPγS to crude HL60 cytosolic preparations by GTPγS as measured on [$^3$H] $PIP_2$ coated 96-well phospholipid FlashPlates®. Various amounts of HL60 cytosol protein were added to individual wells containing 0.2 ml 50 mM HEPES-NaOH, pH 6.7, 0.15 M KCl, 0.1 mM $CaCl_2$, 0.1 mM EGTA, 0.04% deoxycholate (wt/vol) either in the presence or absence of 0.2 mM GTPγS. The release of radioactivity was monitored on a Packard TopCount®.

FIG. 4 is a graph illustrating the release of intracellular PLC activity from streptolysin S permeabilized A431 human carcinoma cells as measured on [$^3$H] $PIP_2$ coated 96-well phospholipid FlashPlate®. Aliquots of resuspended A431 cells were distributed into wells containing 50 mM HEPES-NaOH, pH 6.7, 0.15 M KCl, 0.1 mM $CaCl_2$, 0.1 mM EGTA, 0.04% deoxycholate (wt/vol), 10 units/ml streptolysin S and the volume adjusted to 0.2 ml with reaction buffer. The release of radioactivity was monitored on a Packard TopCount®.

DETAILED DESCRIPTION OF THE INVENTION

Figure 1:
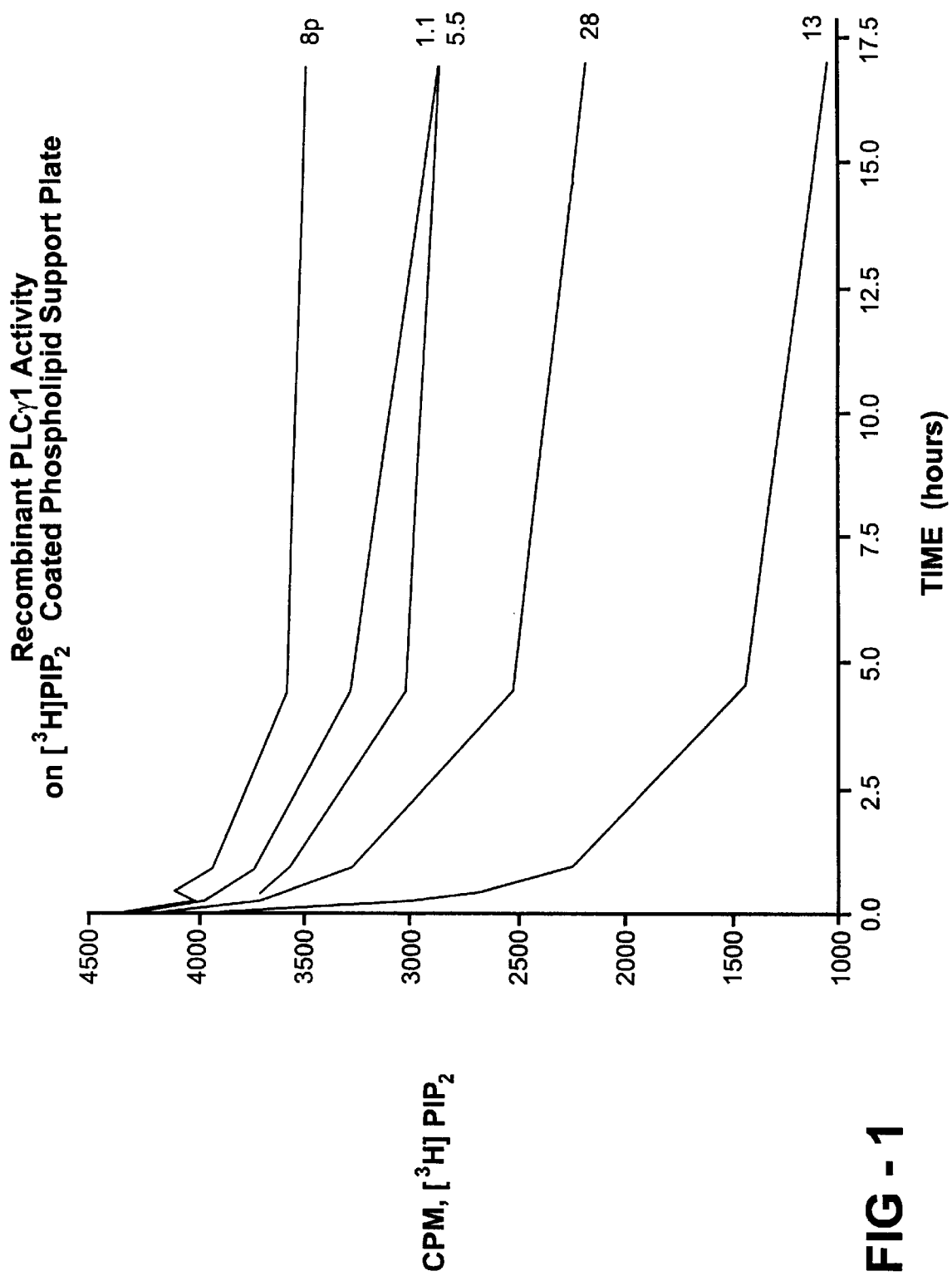
FIG. 1 is a graph illustrating kinetic activity of various amounts of purified recombinant PLC γb 1on [$^3$H] $PIP_2$ coated 96-well phospholipid FlashPlate®. Different concentrations of purified recombinant PLC were added to individual wells in 0.1 ml of 50 mM $NaP_i$, pH 6.7, 0.1 M NaCl, 0.1 mM $CaCl_2$, 0.1 mM EGTA and the release of radioactivity was monitored as a function of time on a Packard TopCount®. (Microplate Scan System manufactured by the Packard Instrument Company of Meriden, Conn.).

The present invention is directed to the use of covalent binding technology to affix an interactive material onto a support body. By the use of a covalent bond, the interactive material is firmly and reliably retained. While the invention may be used to affix a variety of materials to a variety of different substrates for various purposes, it has very significant utility in the fabrication of assay materials, and has particular utility in those instances where the assay materials include a scintillator in the support body, since the covalent binding technology of the present invention does not interfere with the scintillator. The covalent binding material, referred to herein as a linker material has at least one reactive site which can form a covalent bond with the interactive material, or which can activate the covalent binding of the interactive material to the support. As such, the covalent binding material may be capable of reacting with such groups as carboxylic acid groups, primary and secondary amines, sulfhydryl groups, hydroxyl groups and aldehyde groups. It is to be understood that in the course of causing the interactive materials to be covalently bonded to the support, molecular structures of the linker materials themselves can be altered. Therefore, when this disclosure refers to an interactive material being covalently bonded to a support by a particular linker material, it is to be understood that that linker material may be chemically altered either by covalently binding to the interactive material itself, or by activating covalent binding directly to the support.

It is notable that the methods of the present invention do not require pretreatment of the support body or interactive material to provide reactive sites thereupon. As such, the present invention is differentiated from prior art processes which require support bodies or interactive materials to be subjected to ionizing radiation or extreme chemical treatments to make them amenable to binding. As such, the present invention represents a significant improvement over prior art processes.

One particularly preferred group of linking materials which covalently bind to interactive materials comprises vinylsulfones, and some specific examples include divinylsulfone and 1,6-hexane-bis-vinylsulfone. Another preferred group of linker materials which activate covalent binding of interactive materials, while not being directly incorporated into the bond, comprise carbodiimides, and a specifically preferred material is 1-ethyl-3-(3-dimethylamino-propyl) carbodiimide. In some instances, the covalent linker material can be photochemically activatable so that initiation of the covalent binding may be accomplished by appropriately irradiating the reagents.

In those instances where the linker covalently binds to the interactive material, the linking material should also function to retain the bound interactive material on the support body. Therefore, the linker material will also chemically or physically bind to the support body. In some instances, such linker materials will be capable of covalently binding to the support. In those instances where the linker material activates the covalent binding of the interactive material, while not participating in the bond, the linker need not be capable of binding to the support; although in some instances, it will do so.

As will be explained in greater detail herein below, in some particular embodiments of the present invention, the interactive materials may comprise lipid materials such as artificial membranes. The interactive materials may also comprise proteins, nucleic acids, other lipids and receptor molecules. In some very particular embodiments described herein below, the interactive materials will include phosphatidylethanolamine, streptavidin, and wheat germ agglutinin.

In accord with another aspect of the present invention, support bodies may be coated with a linker material for later covalent attachment of an interactive material thereto. Such coated supports will in and of themselves constitute a stock product, and can be sold for later use.

The unique features of this invention will be discussed with regard to a particular type of assay which employs an interactive material bound to a support so as to provide for a substrate of an enzyme. This assay allows the study of enzyme activity in samples without the need to extract the reaction products. The assay embodying the invention can be used in either homogeneous or heterogeneous assay formats and can employ either radiometric or non-radiometric detection methods. With appropriate substrate design, the present invention can be used to study a variety of enzymes, such as phospholipases, for which the assay methods otherwise require extraction steps. Enzyme substrates suitable for use in the invention include, but are not limited to phospholipids, sphingolipids, and any other amphipathic molecules, such as glycosyldiacylglycerols, ceramides, gangliosides, and complex phospholipids like cardiolipin. The enzyme used can be purified, semi-purified or a crude extract. It is to be understood that while the invention is being described with regard to this specific type of assay, it can be employed to bind other types of materials to other supports for use in assays or otherwise.

An amphipathic enzyme substrate labeled on a polar moiety is incorporated by hydrophobic interactions into any suitable hydrophobic layer, such as a lipid layer, that is formed on a solid support and is retained by hydrophobic interaction and/or by covalent attachment. A suitable hydrophobic layer is one that incorporates a component that binds the amphipathic substrate by hydrophobic interaction. The particular substrate to use is designed or selected for its susceptibility to the action of the enzyme of interest and an appropriate location for the label. Suitable reporter group(s) used to label the substrate include, but are not limited to radioactive isotopes, enzymes, fluorogenic, calorimetric, magnetic, chemiluminescent or electrochemical materials or a member of a specific binding pair.

Suitable solid phase supports include but are not limited to synthetic polymer supports such as polystyrene, polypropylene, substituted polystyrene, e.g., laminated or carboxylated polystyrene; polyacrylamides; polyamides; polyvinylchloride, etc.; glass beads; agarose; nitrocellulose; nylon; polyvinylidenedifluoride; surface-modified nylon, etc. Homogeneous assay methods for phospholipases employing a 96-well FlashPlate as the solid support have been shown to work well. (A FlashPlate is a 96-well white polystyrene microplate in which the interior of each well is coated with a thin layer of polystyrene-based scintillant.)

It will thus be seen that the present invention is directed to a method and material for carrying out rapid, enzyme based assays. The assays may be quantitative or qualitative, and do not require extensive sample preparation or extraction steps. The assays rely upon the use of an amphipathic substrate which is reactive with the enzyme. The amphipathic substrate includes a hydrophilic portion which carries a reporter moiety (also referred to as a label), and a hydrophobic portion.

In a typical assay, a sample of material, including the suspected target enzyme, is placed in contact with the hydrophobic layer, which as previously noted is preferably disposed upon a support. The sample is disposed in a polar solvent which typically comprises water, and at least a portion of the enzyme which is in the sample will interact with the substrate material therein. This interaction results in a cleavage of the substrate, which releases a hydrophilic fragment including the reporter material thereupon. The hydrophilic fragment has a low affinity for the hydrophobic layer, and migrates into the exterior, polar solvent. Detection of the reaction is most preferably accomplished by measuring the residual reporter activity of the hydrophobic layer, and this residual reporter activity will be inversely proportional to the activity of the enzyme in the sample. Alternatively, enzyme activity may be measured by detecting the reporter label fragments in the aqueous material.

As noted hereinabove, the reporter moiety may comprise a radioactive species such as tritium, and in some instances, the hydrophobic layer may be disposed upon a support which includes a scintillator material therein. In other instances, the reporter material may comprise a magnetically labeled material, a fluorescent labeled material, a member of an antibody/antigen pair, a fluorescent agent, a color forming agent, a chemiluminescent material, an enzyme different from the target enzyme of the assay, an electrochemically active material, or the like, and other such reporter materials will be apparent to one of skill in the art.

The following examples are intended to illustrate the invention.

COMPARATIVE EXAMPLE I

Sphingomyelinase Assay

In this example, non-covalent binding is used to retain a lipid layer on a support plate.

Preparation of Enzyme Substrate

FlashPlates coated with streptavidin were obtained from NEN® Life Science Products. Biotinylated phosphatidylethanolamine (PE) (Avanti) was diluted to 10 micrograms/mL in PBS (0.1 M NaCl in 0.01 M sodium phosphate buffer, pH 7.4) and 0.1 mL was added to each well. After incubation overnight at room temperature to allow binding to the streptavidin, the remaining solution was removed from the wells by aspiration. Sphingomyelin (egg), [choline methyl-$^3$H] (NEN® Life Science Products, Inc.) was diluted to 1.0 microcurie/mL with Tris-HCl, pH 7.0 containing 0.1% bovine serum albumin [BSA] and 0.1 mL was added to each well. During overnight incubation at room temperature, the sphingomyelin hydrophobically interacted with the PE to form a $^3$H-labeled solid-phase lipid layer. Plates were then aspirated and air-dried.

Enzyme Assay

Sphingomyelinase (Sigma) was serially diluted in PBS containing 1 mg/mL $CaCl_2$ and 1 mg/mL $MgCl_2$ (BioWhittaker) and 0.1 mL was added to each well and incubated overnight at room temperature. The hydrophilic $^3$H-labeled fragment cleaved from the sphingomyelin by the activity of sphingomyelinase moved from the hydrophobic solid-phase lipid layer into the aqueous solution, decreasing the amount of $^3$H within sufficient proximity of the scintillant to be counted. The results in Table 1 show that increasing the amount of sphingomyelinase produced a decrease in the amount of radioactivity detected in the well. The well with no sphingomyelinase was used as a negative control.

TABLE 1

| Sphingomyelinase (mU/mL) | Counts per Minute (CPM) | Percent of Negative Control |
|---|---|---|
| 2000 | 1038 | 8.6 |
| 200 | 2144 | 17.7 |
| 20 | 4672 | 38.6 |

TABLE 1-continued

| Sphingomyelinase (mU/mL) | Counts per Minute (CPM) | Percent of Negative Control |
|---|---|---|
| 2 | 8933 | 73.8 |
| 0.2 | 10691 | 88.4 |
| 0 | 12099 | 100.0 |

COMPARATIVE EXAMPLE II

Phospholipase C Assay

Preparation of Enzyme Substrate

FlashPlates were prepared exactly as in Example 1 except that $PIP_2$, [inositol-2-$^3$H(N)] (NEN® Life Science Products) was added instead of sphingomyelin-[$^3$H] in the preparation of a $^3$H-labeled solid-phase lipid layer.

Partial Purification of PLC (Camps et al. 1992; Camps et al. 1990; Glorschik et al. 1989). For maintenance, HL-60 cells (ATCC CCL-240) were cultured in 1-liter spinner flasks at 10% $CO_2$ in Iscove's Medium supplemented with 20% fetal bovine serum (FBS), 1% L-glutamine and 0.1% gentamicin. To induce phospholipase C, the cells were cultured in media supplemented with 1.25% dimethylsulfoxide (DMSO) for five days, or until a density of about $2–3 \times 10^6$ viable cells was reached. After harvesting by centrifugation and washing twice with wash buffer (20 mM Tris-HCl (pH 7.5)), 1 mM EDTA, 1 mM dithiothreitol, 3 mM benzamidine, 1 mM leupeptin, 1 mM phenylmethyl sulfonyl fluoride (PMSF) and 0.002 mM soybean trypsin inhibitor), the final pellet containing about $2 \times 10^{10}$ cells (30 mL packed cell volume) was resuspended in 50–100 mL of Lysis Buffer (250 mM sucrose, 20 mM Tris-HCl [pH 7.5], 1.5 mM $MgCl_2$, 1 mM ATP, 3 mM benzamidine, 0.001 mM leupeptin, 1 mM PMSF, 0.002 mM soybean trypsin inhibitor). The cells were lysed by four treatments in the cold for one minute each with a Polytron homogenizer with a one minute rest between treatments, followed by sonication in an ice bath four times for one minute with a one minute rest between treatments. The lysate was supplemented with EGTA to 1.25 mM, and debris was removed by a 4° C. centrifugation at 1445×g for twenty minutes. The resulting supernatant was centrifuged at 4° C. for twenty minutes at 17,593×g. The supernatant from this step was centrifuged at 4° C. for sixty minutes at 112,594×g. The final supernatant (cytosol) was passed through a 0.45 micrometer pore size filter. After determination of the protein concentration, the cytosol was snap frozen and stored at −80° C., until used as a source of phospholipase C.

Enzyme Assay

To assay phospholipase C activity, the thawed HL-60 cytosol was diluted to various protein concentrations with PBS containing 0.4 mM $CaCl_2$ and 0.21 mM GTP-gamma-S. Diluted cytosol (0.1 mL) was added to each FlashPlate® well containing a solid-phase lipid layer with $PIP_2$-[$^3$H], and incubated overnight at room temperature. The hydrophilic $^3$H-labeled fragment cleaved from the $PIP_2$ by the activity of phospholipase C moved from the hydrophobic solid-phase lipid layer into the aqueous solution, decreasing the amount of $^3$H label within sufficient proximity of the scintillant to be counted. The results in Table 2 show that increasing the amount of phospholipase C produced a decrease in the amount of radioactivity detected in the well. The well with no phospholipase C was used as a negative control.

TABLE 2

| Phospholipase C (mg/mL of HL-60 cytosol protein) | Counts per Minute (CPM) | Percent of Negative Control |
| --- | --- | --- |
| 3.5 | 864 | 31.1 |
| 1.0 | 1072 | 38.5 |
| 0 | 2782 | 100 |

EXAMPLE III

Covalent Linkage of Phosphatidylethanolamine

In this example, the covalent binding chemistry of the present invention is employed.

Two types of chemistries are involved: one employing divinylsulfone (DVS) and the other using 1-3-(3-dimethylaminopropyl)carbodiimide (EDAC). DVS is generally reactive with amines, sulfhydryl and hydroxyl groups; and, EDAC is reactive with carboxyl groups and hydroxyl groups.

Divinylsulfone Plate Activation

A 1% DVS solution is prepared in 0.1 M sodium carbonate, pH 11.5, immediately prior to use. Aliquots (0.2 ml) are distributed to individual wells and the plate allowed to stand at room temperature for at least thirty minutes. The plate is then washed thrice with 0.1 M sodium carbonate, pH 10.5, and then air dried briefly prior to adding the lipid. A 25 µg/ml solution of phosphatidylethanolamine (PE) is made in 25–50 mM sodium carbonate, pH 9.8–10.2 and 0.2 ml distributed to each well. The plate is incubated again at room temperature for at least three hours. Finally, the plate is washed twice with phosphate buffered saline (PBS), 0.04% deoxycholate and twice with PBS alone. The plate is then air dried and stored in a sealed bag in the dark at room temperature. The coated plates are storage stable for at least six months.

EDAC Plate Activation

A solution of 0.5 mg/ml EDAC is prepared in 10–50 mM MES, pH 6.8–7.2, containing 25 µg/ml of PE and 0.2 ml is distributed to individual wells. The plate is allowed to stand overnight at room temperature in the dark. Finally, the plate is washed twice with phosphate buffered saline (PBS), 0.04% deoxycholate and twice with PBS alone. The plate is then air dried and stored in a sealed bag in the dark at room temperature.

EXAMPLE IV

Covalent Linkage of Streptavidin

A 1% DVS solution is prepared in 0.1M sodium carbonate, pH 11.5, immediately prior to use. Aliquots (0.2 mL) are distributed to individual wells and the plate is allowed to stand at room temperature for at least 15 minutes. The plate is then washed thrice with 0.1M borate, pH 9.2, and then air-dried briefly prior to adding the streptavidin. A 5–50 ug/mL solution of streptavidin is made in 25–50 mM sodium carbonate, pH 9.8–10.2 and 0.2 mL distributed to each well. The plate is incubated again at RT for at least three hours. Finally the plate is washed twice with PBS containing 0.02% Tween-20 and twice with PBS alone. The plate is then air-dried and stored in a sealed bag in the dark at RT.

EXAMPLE V

Covalent Linkage of Wheat germ Agglutinin (WGA)

A solution of 0.5 mg/mL EDAC is prepared in 10-mM MES, pH 5.2–7.2, containing 25 ug/mL of WGA. Aliquots (0.2 mL) are distributed to individual wells and the plate is allowed to stand at room temperature overnight in the dark. The plate is then washed twice with PBS containing 0.02% Tween-20 and twice with PBS alone. The plate is then air-dried and stored in a sealed bag in the dark at RT.

Performance Evaluation of Assay Plates

Inositol specific phospholipase Cs (PLCs) are key enzymes in the signal transduction of many cell mediated responses as diverse as peptide hormones and neurotransmitters (Rhee and Choi, 1992). These enzymes are specific hydrolases for the phosphoinositide. The enzyme reaction of the PLCs with phosphatidylinositol 4,5-bisphosphate (PIP$_2$) results in the production of inositol 1,4,5-trisphosphate (IP$_3$) and diacylglycerol. It is the generation of these products that produces the cascade of regulatory signals throughout the cell. IP$_3$ induces the intracellular release of Ca$^{2+}$ stores from the endoplasmic reticulum through its specific interactions with the IP$_3$ receptor, whereas, diacylglycerol is a potent activator of protein kinase C. The activation of these cellular events results in a stimulation of a series of pathways that modulate cellular activity.

Classically, PLC enzymes are divided into three families designed β, δ and γ. The β and γ are regulated either through the G-protein coupled pathway or the receptor mediated tyrosine kinase pathway, respectively. Activity of these enzymes has been historically studied using solution based assays with phospholipid vesicles containing trace amounts of [$^3$H, inositol] PIP$_2$ (DeVivo, 1994). The hydrolytic reaction is monitored by the addition of acidified organic solvents and subsequent phase separation. [$^3$H] IP$_3$ remains in the aqueous phase while the acidic labeled lipids partition into the organic layer. Thus, simple radioassays of the aqueous layer provide a convenient way to measure PLC activity. However, the limits of the assay are that it is not readily amenable to high-throughput screening (HTS) methods.

In order to study these enzymes in high throughput fashion, a method was developed for monitoring PLC activity on FlashPlates® containing bound [$^3$H] phosphatidylinositol 4,5-bisphosphate. The FlashPlate® was modified in order to capture labeled phospholipids onto the surface and, thereby, provide a functional substrate to gauge PLC activity.

Methods

Phospholipid modified FlashPlates® were made by a variety of different methods in order to test various coating surfaces. Ninety-six well Phospholipid FlashPlates® were coated with 0.2 ml of a solution containing [1-$^3$H, inositol] PIP$_2$ (~20 Ci/mmol, NEN) at concentrations between 0.25–1 µCi/ml for at least three hours. The wells were then washed twice with phosphate buffered saline (PBS) containing 0.04% sodium deoxycholate and finally with PBS alone. Typically, coefficient of variation ranged between 8–12%. Reactions were conducted directly in the wells in buffer indicated in the legends and monitored on a Packard Top-Count® instrument.

One unit of PLC activity is defined as one nmol of [$^3$H] IP$_3$ formed per minute per mg of enzyme using typical solution based assays (DeVivo, 1994).

HL60 cells were grown to late log phase prior to harvest and the cytosolic fraction prepared as previously described (Camps et al. (1990; Camps et al. 1992) or HL60 cytosolic extracts were purchased commercially from ABS, Inc. A431 human epidermoid carcinoma cells were grown in 150 cm$^2$ culture flasks containing Dulbecco's modified Eagle's medium (DMEM) with 10% fetal calf serum (FCS) prior to harvesting. A431 cells were cultured until ~50% confluency was reached. Cells were harvested by scraping the attached cell mass from the bottom of the flask and pelleting by low speed centrifugation. Cell pellets were then rinsed twice with PBS. Cells were resuspended in a minimal volume of reaction buffer containing 10 units/ml streptolysin S and counted prior to being aliquoted to individual wells.

All other chemicals or reagents were of reagent grade or better.

Results

Our initial work served to verify that the labeled surface of the Phospholipid FlashPlate® could effectively present the inositol headgroup to the enzyme for hydrolysis. Over the course of the 17.5 hour reaction purified recombinant PLC γ1 displayed an ability to release bound counts in a concentration dependent fashion (see FIG. 1). In all instances the reaction of PLC γ1 plateaued within the first five hours of the reaction and produced very little release of counts thereafter. At the highest concentration of enzyme tested, 130 μg, over 75% of the radioactivity was released from the plate surface. These results indicated that the majority of the surface bound [$^3$H] $PIP_2$ is readily available as a substrate for the enzyme. In order to verify that the release of surface bound counts was in fact due to hydrolysis of the [$^3$H] $PIP_2$ individual wells were aspirated and extracted with two volumes of chloroform-methanol under acidic conditions ($CHCl_3$:$CH_3OH$:HCl, 2:1:0.01). The relative distribution of radioactivity in the organic and aqueous phase represents labeled $PIP_2$ and $IP_3$, respectively. As shown in Table 3, release of radioactivity from the labeled Phospholipid FlashPlate® was due predominantly to the hydrolysis of the bound [$^3$H] $PIP_2$ with both crude PLC preparations from HL60 cytosolic extracts and recombinant PLC (control wells showed little or no release of radioactivity, data not shown). In both instances, the radioactivity was distributed mostly into the aqueous phase (~90% and above) indicative of [$^3$H]$IP_3$. This result shows that labeled $IP_3$ was being specifically released from the Phospholipid FlashPlate® and that surface bound labeled $PIP_2$ was in fact a viable substrate for both crude enzymatic PLC preparations of HL60 cytosolic extracts, as well as the purified recombinant PLC.

TABLE 3

Post-reaction Organic Extraction of Aqueous Samples from Individual Wells of [$^3$H] $PIP_2$ Coated Phospholipid FlashPlate®

| Sample (# of experiments) | % Distribution | |
| --- | --- | --- |
| | Aqueous Phase ([$^3$H]$IP_3$) | Organic Phase ([$^3$H] $PIP_2$) |
| HL60 cytosol (n = 10) | 89 ± 7.5% | 11 ± 1.1% |
| Recombinant PLC (n = 3) | 97 ± 0.3% | 3 ± 0.15% |

Figure 2A:
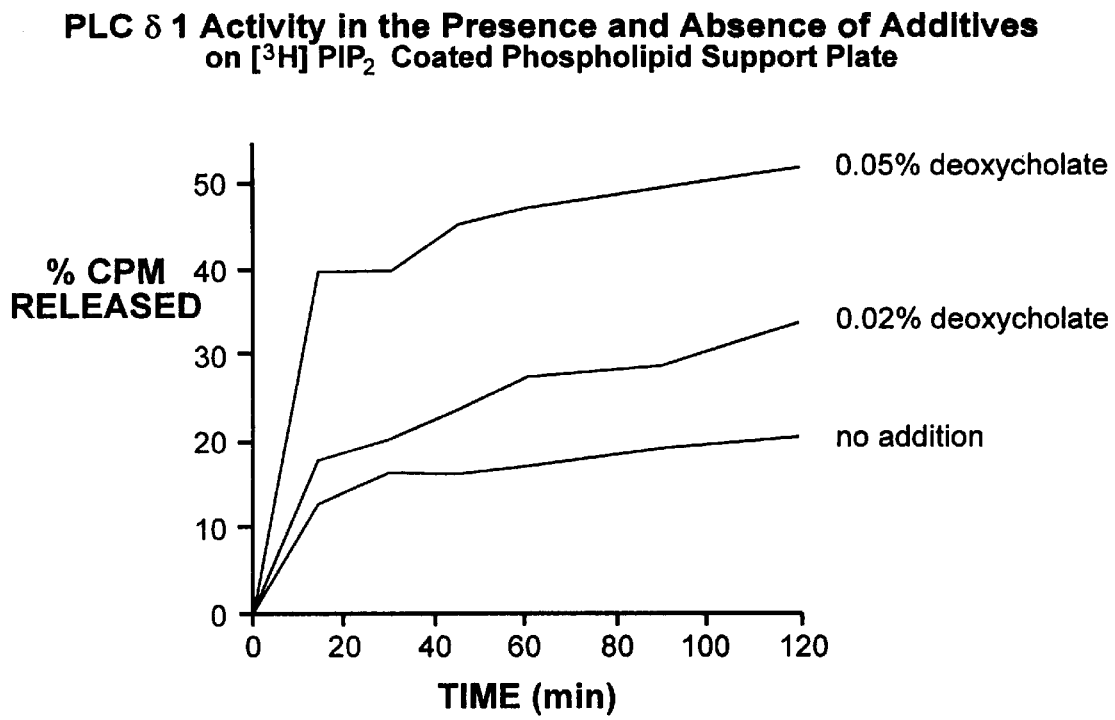
FIG. 2A is a graph illustrating the effects of additives to PLC δ1 activity against [$^3$H] $PIP_2$ coated 96-well phospholipid FlashPlate® wherein the effects of different concentrations of deoxycholate on the release of radioactivity as a function of time by 13 mU PLC in 0.2 ml HEPES-NaOH, pH 7.0, 0.14 M KCl, 0.1 mM $CaCl_2$, 0.1 mM EGTA, [deoxycholate]'s on a % (wt/vol) basis.
Figure 2B:
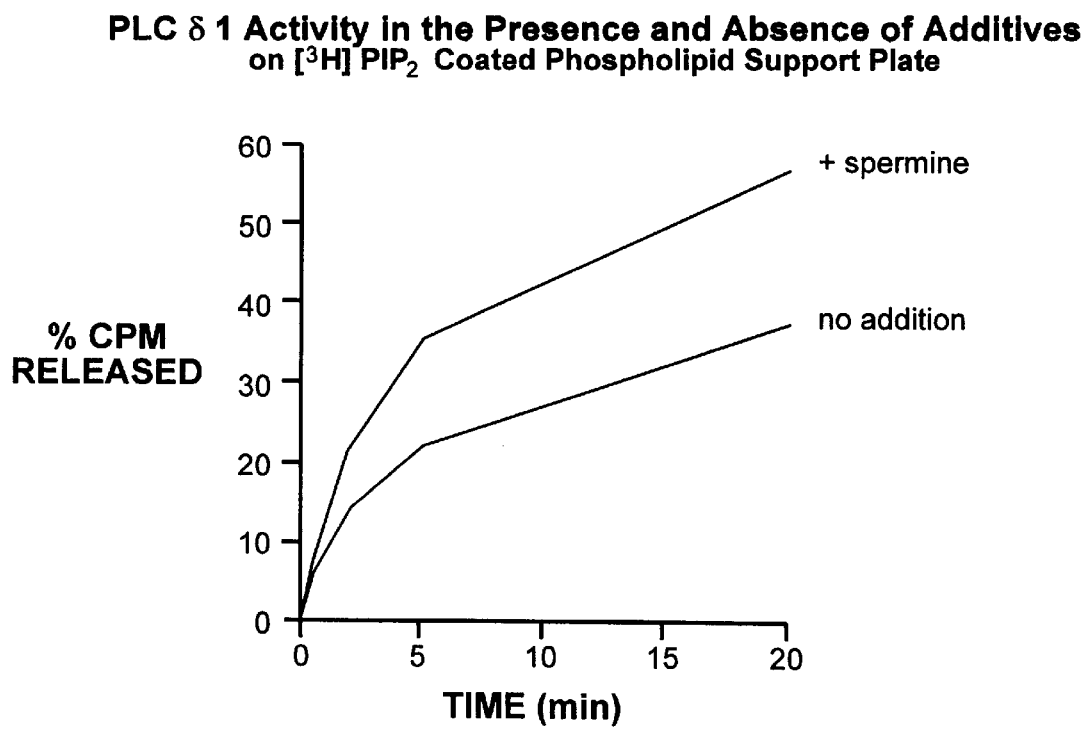
FIG. 2B is a graph illustrating the effect of the addition of 0.2 mM spermine on 100 mU PLC activity in 0.2 ml 50 mM HEPES-NaOH, pH 6.7, 0.15 M KCl, 0.1 mM $CaCl_2$, 0.1 mM EGTA, 0.04% deoxycholate (wt/vol). The release of radioactivity was monitored on a Packard TopCount®.

The reaction also displayed many of the same characteristics as had previously been shown for solution based assays using mixed micelles in the presence of either deoxycholate (Crooke and Bennett, 1989) or spermine (Haber et al., 1991). For these assays recombinant PLC δ1 showed enhanced hydrolytic activity in a concentration dependent manner upon addition of sodium deoxycholate (see FIG. 2A) or in the presence of added spermine (see FIG. 2B). The results confirm the effects of these compounds on the stimulation of PLC activity as had been previously published (Crooke and Bennett, 1989; Haber et al. 1989) and validate the utility of the plate format when compared to solution based micelle assays.

Other experiments were designed to explore whether the stimulation of PLC activity from crude cellular extracts could be monitored on the Phospholipid FlashPlate® using previously described protocols (Rhee and Choi, 1992; DeVivo 1994). Various protein concentrations of HL60 cytosolic extracts were treated in the presence or absence of the non-hydrolyzable analog GTPγS and the decrease of radioactivity was monitored kinetically. As shown in FIG. 3, in the absence of the analog the release of bound counts displayed a concentration dependence upon the amount of protein added and the reaction began to taper off by three hours at ~15%. Addition of GTPγS to the samples produced a stimulation in PLC activity at every protein concentration tested. However, the concentration dependence of added protein appeared to be lost possibly due to the fact that only low substrate levels were available on the surface. Even despite this, a clear 2–3 fold stimulation was evident for each protein concentration used.

As a further test of this format, we analyzed the activity of PLC as released from permeabilized A431 human epidermoid carcinoma cells (see FIG. 4). In this instance, addition of various amounts of cells to the [$^3$H] $PIP_2$ coated Phospholipid FlashPlate resulted in the release of radioactivity in a cell number dependent manner. Cell numbers at and below $2 \times 10^5$ cells/ml showed an initial lag phase on the reaction indicating a delay in the release of PLC activity from the cells. Moreover, at cell numbers about $2 \times 10^5$ cells/ml the release of radioactivity from the surface could be shown to be due to the release of both intact lipid and $IP_3$ (data not shown). Therefore, at elevated cell numbers this result suggests that other cellular components are capable of removing the lipid from the surface in a non-hydrolytic reaction. Cumulatively these results demonstrate that PLC activity can be monitored from both permeabilized cells and cytosolic extracts in a high throughput fashion on [$^3$H] $PIP_2$ Coated Phospholipid FlashPlates®.

Conclusions

This work clearly demonstrates the utility of [$^3$H] $PIP_2$ coated phospholipid FlashPlates® for monitoring PLC activity for high throughput screening of receptor-coupled functional assays. The results indicate that PLC activity can be monitored easily from a variety of sources including purified recombinant enzyme preparations to crude cell lysates and permeabilized cells. Moreover, this format provides a surface comparable to that used for classical labeled micelle studies and illustrates the feasibility of this assay for measuring PLC activity in a variety of different drug screening assays.

While the present invention has been illustrated with regard to some specific type of assays, it is to be understood that is has broader applicability for covalently binding a variety of materials to support bodies.

The principles of the present invention may thus be adapted to a variety of applications, any number of which will be apparent to one of skill in the art. In view of the foregoing, it will be understood and appreciated that numerous modifications and variations of the aforedescribed invention may be readily implemented. The discussion, description and examples set forth herein are illustrative of particular embodiments of the present invention but are not meant to be limitations upon the practice thereof. It is the following claims, including all equivalents, which define the scope of the invention.

Literature Cited

Camps et al. (1992) *Eur. J. Biochem.* 206:821–831.

Camps et al. (1990) *Biochem. J* 271:743–748.

Crooke and Bennett (1989) *Cell Calcium*, 10:309–23.

De Vivo (1994) Assays for G-protein regulation of phospholipase C activity. *Methods in Enzymology* 238:131–141.

Gierschik et al. (1989) *Eur. J. Biochem.* 183:97–105.

Haber et al. (1991) *Arch. Biochem. Biophys.*, 288(1) :243–6.

Hianik et al (1996) Immobilization of enzymes on lipid bilayers on a metal support allows study of the biophysical mechanisms of enzymatic reactions. *Bioelectrochemistry and Bioenergetics* 41:221–225.

Hoekstra and Duzgunes (1993) Lipid mixing assays to determine fusion in liposome systems. *Meth. Enz.* 220:15–32.

Larsson et al. (1987) Covalent binding of proteins to grafted plastic surfaces suitable for immunoassays. *Journal of Immunological Methods* 98 129–135.

Miller and Racker (1976) *J Membr. Biol.* 26:319.

Mueller et al. (1962) *Circulation* 26:1167.

Ottova and Tien (1997) Self-assembled bilayer lipid membranes: from mimicking biomembranes to practical applications. *Bioelectrochemistry and Bioenergetics* 42:141–152.

Rhee and Choi (1992) *J. Biol. Chem.*, 267(18):12393–6.

Wright and Huang (1992) Bilayer stabilization of phosphatidylethanolamine by N-biotinylphosphatidylethanolamine. *Biochim. Biophys. Acta* 1103:172–178.

We claim:

1. In an assay member comprising a support body having an interactive material retained thereupon, wherein the improvement comprises in combination:

said interactive material being covalently bonded to the support body by a linker material.

2. The assay member as in claim 1, wherein said support body includes a scintillator material therein.

3. The assay member as in claim 2, wherein said scintillator material is a polystyrene based scintillator material.

4. The assay member as in claim 1, wherein said linker material forms a covalent bond to the support body.

5. The assay member as in claim 1, wherein said linker material is a photochemically activatable linker material characterized in that said linker material, upon photochemical activation, forms a covalent bond to either said interactive material, or to said support body.

6. The assay member as in claim 1, wherein said interactive material comprises a binding pair member.

7. The assay member as in claim 6, wherein said binding pair member is selected from the group consisting of proteins, nucleic acids, lipid structures, receptors, and carbohydrates.

8. The assay member as in claim 1, wherein said interactive material is selected from the group consisting of phosphatidylethanolamine, streptavidin, wheat germ agglutinin, DNA, RNA, and combinations thereof.

9. The assay member as in claim 1, wherein said linker material covalently binds to said interactive material.

10. The assay member as in claim 1, wherein said linker material activates the covalent binding of said interactive material to said support body.

11. The assay member as in claim 1, wherein said linker material comprises a compound which is capable of reacting with moieties selected from the group consisting of —COOH, SH, OH, primary amines, secondary amines, aliphatic hydrocarbons, aromatic hydrocarbons, and combinations thereof.

12. The assay member as in claim 1, wherein said linker material is selected from the group consisting of vinylsulfones, carbodiimides, photo reactive compounds, and combinations thereof.

13. The assay member as in claim 1, wherein said linker material is selected from the group consisting of divinylsulfone, 1-ethyl-3-(3-dimethylamino-propyl) carbodiimide, 1,6-hexane-bis-vinylsulfone, and combinations thereof.

14. An assay member comprising:

a support body which includes a scintillator material;

a linker material comprising a member selected from the group consisting of vinylsulfones, carbodiimides and photoreactive compounds; and an interactive material covalently bonded to said support body by a covalent bond formed through the interaction of said linker material with said interactive material or said support body, said interactive material selected from the group consisting of phosphatidylethanolamine, streptavidin, wheat germ agglutinin, DNA, RNA, and combinations thereof.

15. A method of the manufacture of an assay member said method including the steps of:

providing a support body;

providing an interactive material;

providing a linker material, said linker material being capable of covalently binding said interactive material to said support body; and binding said interactive material to said support body whereby said interactive material is retained upon said support body by a covalent bond.

16. The method as in claim 14, wherein said support body includes a scintillator material therein.

17. The method as in claim 15, wherein said interactive material is selected from the group consisting of proteins, nucleic acids, lipid structures, receptors, carbohydrates, and combinations thereof.

18. The method as in claim 15, wherein said interactive material is selected from the group consisting of phosphatidylethanolamine, streptavidin, wheat germ agglutinin, DNA, RNA, and combinations thereof.

19. The method as in claim 15, wherein the step of providing a linker material comprises providing a photochemically activatable material; and the step of binding said interactive material to said support body includes the step of photochemically activating said linker material.

20. The method as in claim 15, wherein the step of providing a linker material comprises providing a linker material selected from the group consisting of vinylsulfones, carbodiimides, photoreactive compounds, and combinations thereof.

21. The method as in claim 15, wherein the step of binding said interactive material to said support body comprises binding said interactive material to said support body without having modified the surface of the interactive material or the support body.

22. In an assay member comprising a support body having an interactive material retained thereupon, wherein the improvement comprises in combination:

said interactive material being covalently bonded to said support body by a linker material, and said support body being further characterized in that the support is not subjected to any surface modification prior to the interactive material being covalently bonded thereto.

* * * * *